United States Patent
Stapert et al.

(10) Patent No.: US 11,369,340 B2
(45) Date of Patent: Jun. 28, 2022

(54) TRACKING A FEATURE OF AN INTERVENTIONAL DEVICE

(71) Applicant: KONINKLIJKE PHILIPS N.V., Eindhoven (NL)

(72) Inventors: Hendrik Roelof Stapert, Rosmalen (NL); Mustafa Hakan Gökgürler, Helmond (NL); Jeroen Kortsmit, Son en Breugel (NL); Stefan Van De Pas, Herten (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 382 days.

(21) Appl. No.: 16/337,230

(22) PCT Filed: Sep. 29, 2017

(86) PCT No.: PCT/EP2017/074905
§ 371 (c)(1),
(2) Date: Mar. 27, 2019

(87) PCT Pub. No.: WO2018/060499
PCT Pub. Date: Apr. 5, 2018

(65) Prior Publication Data
US 2019/0261944 A1 Aug. 29, 2019

(30) Foreign Application Priority Data
Sep. 30, 2016 (EP) .................... 16191651

(51) Int. Cl.
*A61B 5/06* (2006.01)
*A61B 8/00* (2006.01)
(Continued)

(52) U.S. Cl.
CPC ............ *A61B 8/0841* (2013.01); *A61B 5/066* (2013.01); *A61B 8/12* (2013.01); *A61B 8/4245* (2013.01);
(Continued)

(58) Field of Classification Search
CPC ..... A61B 8/0841; A61B 8/445; A61B 8/4477; A61B 8/5246; A61B 8/4245; A61B 5/066;
(Continued)

(56) References Cited

U.S. PATENT DOCUMENTS 4,249,539 A 2/1981 Vilkomerson
10,869,650 B2 * 12/2020 Hill ..................... A61B 8/085
(Continued)

FOREIGN PATENT DOCUMENTS

WO 2011138698 A1 11/2011
WO WO-2014138652 A1 * 9/2014 ............ A61B 5/062
(Continued)

*Primary Examiner* — Christopher Koharski
*Assistant Examiner* — Remy C Cooper (57) ABSTRACT

The present invention relates to a system for indicating a position of an interventional device feature (11a) of an interventional device (11) respective an image plane (12) defined by an ultrasound imaging probe (18) of a beam-forming ultrasound imaging system (15) in which the position of the interventional device feature (11a) is determined based on ultrasound signals transmitted between the ultrasound imaging probe (18) and an ultrasound transducer (16) attached to the interventional device at a predetermined distance (Lp) from the interventional device feature (11a). An icon providing unit (IPU) provides a first icon (Cde) indicative of a circular zone with a radius corresponding to the predetermined distance (Lp). The first icon (Cde) is
(Continued)

displayed in a fused image that includes a reconstructed ultrasound image (RUI) from the beamforming ultrasound imaging system.

15 Claims, 5 Drawing Sheets

(51) Int. Cl.
*A61B 8/08* (2006.01)
*A61B 8/12* (2006.01)
*G06T 11/00* (2006.01)

(52) U.S. Cl.
CPC ............ *A61B 8/445* (2013.01); *A61B 8/4477* (2013.01); *A61B 8/463* (2013.01); *A61B 8/483* (2013.01); *G06T 11/003* (2013.01); *A61B 8/469* (2013.01)

(58) Field of Classification Search
CPC ........... A61B 8/12; A61B 8/463; A61B 8/483; A61B 8/469; A61B 8/14; A61B 8/4494; A61B 8/5253; A61B 5/743; G06T 11/003
See application file for complete search history.

(56) References Cited

U.S. PATENT DOCUMENTS

| | | |
|---|---|---|
| 2003/0060700 A1 | 3/2003 | Solf |
| 2014/0187947 A1* | 7/2014 | Hansegard ........... A61B 8/5261 |
| | | 600/440 |
| 2014/0276003 A1 | 9/2014 | Wang |
| 2016/0128668 A1 | 5/2016 | Jain |
| 2016/0242856 A1 | 8/2016 | Jain |
| 2016/0317119 A1* | 11/2016 | Tahmasebi Maraghoosh ............. |
| | | A61B 8/483 |
| 2016/0324501 A1* | 11/2016 | Vignon ................ A61B 8/4254 |
| 2016/0374644 A1* | 12/2016 | Mauldin, Jr. ........ A61B 8/5223 |
| | | 600/424 |
| 2017/0202625 A1* | 7/2017 | Bharat ................. A61B 8/5261 |

FOREIGN PATENT DOCUMENTS

| | | |
|---|---|---|
| WO | 2015101949 A1 | 7/2015 |
| WO | 2016009350 A1 | 1/2016 |

* cited by examiner

TRACKING A FEATURE OF AN INTERVENTIONAL DEVICE

CROSS-REFERENCE TO PRIOR APPLICATIONS

This application is the U.S. National Phase application under 35 U.S.C. § 371 of International Application No. PCT/EP2017/074905, filed on Sep. 29, 2017, which claims the benefit of European Patent Application No. 16191651.5, filed on Sep. 30, 2016. These applications are hereby incorporated by reference herein.

FIELD OF THE INVENTION

The present invention relates to the localization of an interventional device within the ultrasound field of a beamforming ultrasound imaging system. More specifically it relates to the localization of a feature of the interventional device respective an image plane of the beamforming ultrasound imaging system.

BACKGROUND OF THE INVENTION

Interventional devices such as medical needles, catheters and surgical tools are often difficult to visualize in an ultrasound image due to the specular nature of their reflectivity, particularly at unfavorable incidence angles.

In one solution to this problem, U.S. Pat. No. 4,249,539 describes an arrangement in which the tip of a medical needle includes an ultrasound transducer that is responsive to the ultrasound signals emitted by an ultrasound imaging system. Upon detecting an ultrasound pulse from the ultrasound imaging system, a circuit connected to the transducer triggers the insertion of the needle position into the ultrasound image through either the generation of a return ultrasound pulse from the needle tip, or through the simulation of such a return pulse using a time of flight delay.

In other solutions to this problem, patent applications WO2011138698, WO2015101949 and WO2016009350 describe systems for tracking an instrument in an ultrasound field with an ultrasound receiver that is mounted to the instrument. The position of the ultrasound receiver is subsequently displayed in an ultrasound image corresponding to the ultrasound field.

A drawback of the above-mentioned systems arises from the fact that it is the position of the ultrasound transducer that is determined and subsequently displayed in the ultrasound image. Typically a user is interested in the position of a particular feature of the instrument, such as the distal end of a needle, rather than the position of the ultrasound transducer itself. However, the mechanical constraints of such instruments often hampers the ability to position the ultrasound transducer at-will, for example at the tip of a needle where it might interfere with insertion. Another drawback of known localization systems occurs more specifically when they are used in conjunction with a planar ultrasound imaging system. Owing to the separation between the ultrasound transducer being tracked and the feature of the instrument, the ultrasound transducer may be out-of-plane when the feature is in-plane, but poorly visible under ultrasound. Thus it would be beneficial to better indicate the position of a feature of the instrument, such as the tip of a needle, in relation to the ultrasound imaging plane.

SUMMARY OF THE INVENTION

In seeking to alleviate the drawbacks of known localization systems, a system is provided for indicating a position of an interventional device feature of an interventional device respective an image plane defined by an ultrasound imaging probe of a beamforming ultrasound imaging system in which the position of the interventional device feature is determined based on ultrasound signals transmitted between the ultrasound imaging probe and an ultrasound transducer attached to the interventional device at a predetermined distance from the interventional device feature. The system includes an image reconstruction unit that is configured to provide a reconstructed ultrasound image corresponding to an image plane defined by the ultrasound imaging probe. The system also includes a position determination unit configured to compute a position of the ultrasound transducer respective the image plane based on ultrasound signals transmitted between the ultrasound imaging probe and the ultrasound transducer. The system also includes an icon providing unit configured to provide a first icon indicative of a circular zone with a radius corresponding to the predetermined distance between the ultrasound transducer and the interventional device feature. The system also includes an image fusion unit configured to provide a fused image comprising the reconstructed ultrasound image and the first icon. The first icon is centered in the reconstructed ultrasound image at an insertion point corresponding to a projection of the position of the ultrasound transducer onto the image plane.

In so doing, a system is provided which can be used to track the position of the interventional device feature respective the image plane. The center of the first icon represents the position of the ultrasound transducer as-projected onto the image plane. Moreover, the first icon defines a portion of the image plane corresponding to a range of possible positions of the interventional device feature, as illustrated by the following scenarios.

In a first scenario the interventional device feature and the ultrasound transducer both lie in the image plane. Here the fused image includes the first icon which is centered at the position of the ultrasound transducer. The interventional device feature lies somewhere around the perimeter of the circular zone indicated by the first icon; this being because the radius of the circular zone corresponds to the predetermined distance between the ultrasound transducer and the interventional device feature. When only a single ultrasound transducer is attached to the interventional device to track its position the exact radial direction in the fused image along which the interventional device feature is located respective the ultrasound transducer is indeterminable. However, it is known that the feature lies somewhere around the perimeter of the circular zone indicated by the first icon. As described later, this in itself is useful information to a system operator.

In a second scenario the interventional device feature lies in the image plane and the ultrasound transducer lies above or below the image plane along a line passing through the feature and normally with respect to the image plane. Here the fused image includes the first icon which is centered at the position of the ultrasound transducer as-projected onto the image plane. However, now the interventional device feature also lies at the center of the circular zone indicated by the first icon.

In an intermediate scenario the interventional device feature lies in the image plane and the ultrasound transducer is located above or below the image plane along a line passing through the ultrasound transducer and at an acute angle to the image plane. Here the fused image includes the first icon which is centered at the position of the ultrasound transducer as-projected onto the image plane. The interventional device feature now lies somewhere between the center of the circular zone indicated by the first icon and the perimeter of the circular zone. Thus, in the three scenarios described above in which the interventional device feature is in the image plane, the first icon defines a portion of the image plane corresponding to a range of possible positions of the interventional device feature. Because the interventional device feature is known to be within the perimeter of the circular zone defined by the first icon, improved positioning of the interventional device feature respective the image plane is provided. Put another way, a user of the system has confidence that the interventional device feature does not impact image features that lie outside this circular zone. Advantageously the localization can be provided using only a single ultrasound transducer, thereby simplifying manufacture of the interventional device.

In yet another scenario the interventional device feature and the ultrasound transducer both lie outside the image plane. Here the fused image includes a first icon which is centered at the position of the ultrasound transducer as-projected onto the image plane. The interventional device feature now lies within a tubular volume extending either side of the image plane through the perimeter of the first icon. In this scenario, the circular zone indicates a region of the image plane within which the interventional device feature would be positioned if it were subsequently moved into the image plane along the projection direction. Again, improved positioning of the interventional device feature respective the image plane is provided positioning because a user of the system has confidence in where on the image plane the interventional device feature will end up when it meets the image plane.

In-use the above indications of the position of the interventional device feature respective the image plane may be supplemented by a system user's knowledge to more precisely determine its position. For example, partial images of the interventional device trajectory obtained intermittently from ultrasound reflections in the usual way under ultrasound imaging system may allow the user to identify exactly where on the perimeter of the circular zone indicated by the first icon the feature lies. Moreover since a user knows whether the trajectory is roughly in-plane or roughly perpendicular to the image plane, they will know which of the first and second scenarios described above are more applicable.

In accordance with one aspect of the invention the position computed by the position determination unit includes an out-of-plane distance corresponding to a distance between the ultrasound transducer and the image plane. Moreover, the image fusion unit is further configured to provide in the fused image a second icon indicative of a circular zone with a radius that varies in accordance with the out-of-plane distance. When used in combination with the first icon, the variable radius of the second icon can improve the localization of the interventional device feature. Because the radius of the second icon varies in accordance with the out of plane distance, and the radius of the first icon is dependent on the distance between the ultrasound transducer and the interventional device feature, when the interventional device feature and the ultrasound transducer are advanced along a trajectory passing normally through the image plane the circular zones indicated by the first and second icons become equal when the interventional device feature lies in the image plane. Thus, the relative sizes of the first and second icons indicate the proximity of the interventional device feature to the image plane. This aspect of the invention finds particular application in the second scenario outlined above; i.e. in out-of-plane procedures. Substantially the same result is achieved when the trajectory is approximately normal to the image plane, e.g. within ±10 degrees of exactly normal to the image plane. This aspect of the invention also finds application in the first scenario outlined above, i.e. in in-plane procedures in which the interventional device feature and the ultrasound transducer are advanced along a trajectory that lies in the image plane. In such a procedure the circular zone indicated by the second icon has a minimum radius whilst the ultrasound transducer is advanced in the image plane. A user can thus guide the interventional device feature across the image plane by minimizing the radius of the circular zone indicated by the second icon; and moreover the user knows that the interventional device feature lies at the perimeter of the circular zone indicated by the first icon.

In accordance with another aspect of the invention an interventional device is disclosed. The interventional device includes an interventional device feature, an ultrasound transducer and a data carrier. The ultrasound transducer is attached to the interventional device at a predetermined distance from the interventional device feature. The data carrier comprises data representative of the predetermined distance. The data, when received by the icon providing unit of the system, causes the icon providing unit to provide a first icon indicative of a circular zone with a radius corresponding to the predetermined distance between the ultrasound transducer and the interventional device feature. Advantageously, improved determination of the position of the distal end of the interventional device respective the image plane of the beamforming ultrasound imaging system is achieved.

In accordance with another aspect of the invention a computer program product is disclosed. The computer program product may be used in conjunction with the system and the device.

It is to be noted that the various aspects or embodiments described in relation to the system may also be used in combination or isolation with aspects or embodiments of the interventional device, and likewise with aspects and embodiments of the computer program product, and vice versa.

DETAILED DESCRIPTION OF THE INVENTION

In order to illustrate the principles of the present invention, various systems are described in which the position of an interventional device feature, exemplified by the distal end, of an interventional device, exemplified by a medical needle, is indicated respective an image plane defined by a linear array of a 2D ultrasound imaging probe.

It is however to be appreciated that the invention also finds application in determining the position of features of other interventional devices such as a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool, a tissue sealing device, or a tissue cutting device. The tracked features of such interventional devices may exemplarily include a distal end of the interventional device, a biopsy sampling point of the interventional device, a cutting edge of the interventional device, an opening of a channel in the interventional device, a sensor (e.g. for sensing flow, pressure, temperature etc.) of the interventional device, a surgical tool (e.g. a scraper) integrated in the interventional device, a drug delivery point of the interventional device, or an energy delivery point of the interventional device.

Furthermore it is to be appreciated that the exemplified linear array of a 2D ultrasound imaging probe is only one example of an ultrasound transceiver array of a beamforming ultrasound imaging system in which the invention may be used. The invention also finds application in other types of beamforming ultrasound imaging systems whose associated ultrasound transceiver arrays exemplarily include a 2D array of a 3D imaging probe (or in bi-plane view), a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe.

Figure 1:
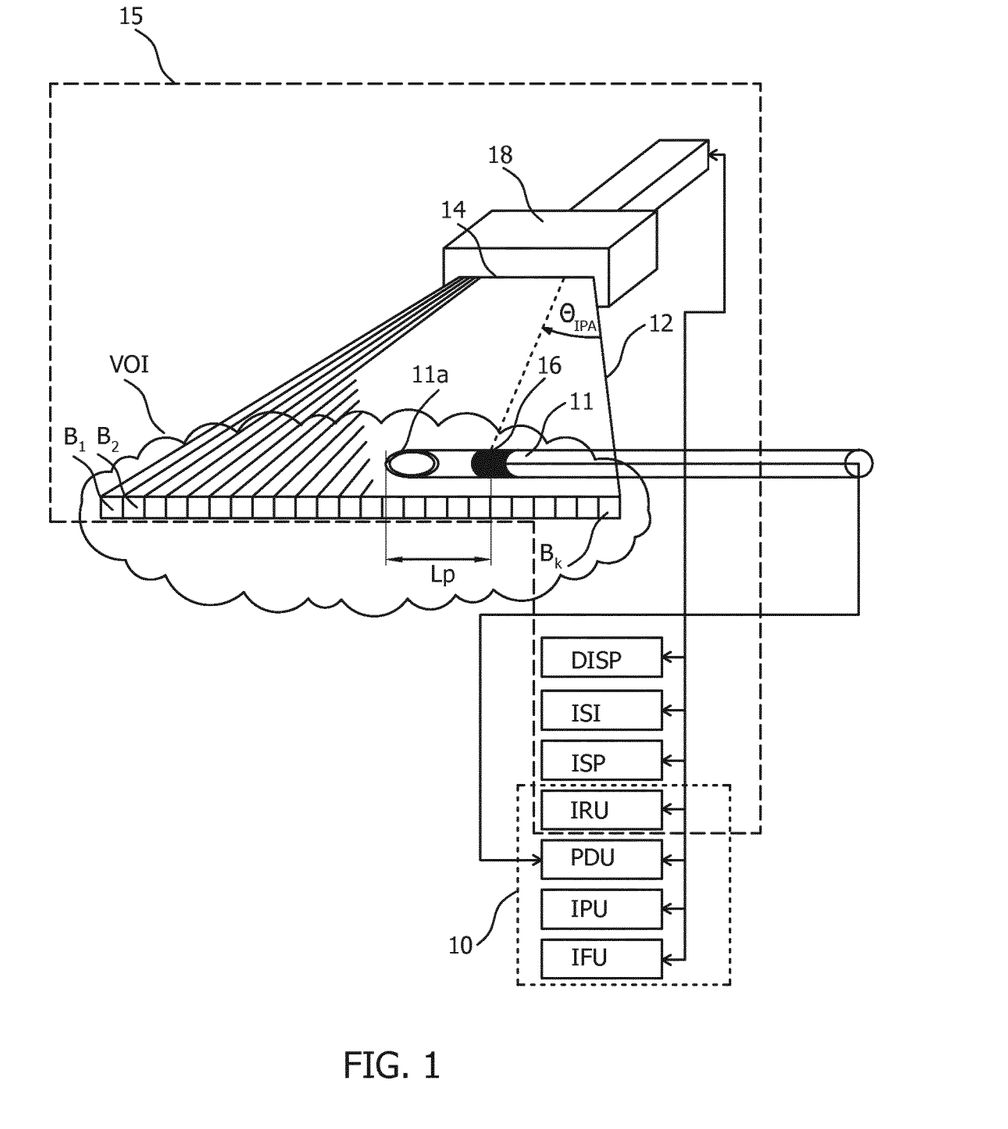
FIG. 1 illustrates a beamforming ultrasound imaging system 15 in combination with an interventional device 11 and a first embodiment of the invention 10.

FIG. 1 illustrates a beamforming ultrasound imaging system 15 in combination with an interventional device 11 and a first embodiment of the invention 10. In FIG. 1, beamforming ultrasound imaging system 15 includes a 2D ultrasound imaging probe 18 which is in communication with image reconstruction unit IRU, imaging system processor ISP, imaging system interface ISI and display DISP. The units IRU, ISP, ISI and DISP are conventionally located in a console that is in wired communication with 2D ultrasound imaging probe 18. It is also contemplated that wireless communication, for example using an optical, infrared, or an RF communication link, may replace the wired link. It is also contemplated that some of units IRU, ISP, ISI and DISP may instead be incorporated within 2D ultrasound imaging probe 18, as in for example the Philips Lumify ultrasound imaging system. In FIG. 1, 2D ultrasound imaging probe 18 includes linear ultrasound transceiver array 14 that transmits and receives ultrasound energy within an ultrasound field that intercepts volume of interest VOI. The ultrasound field is fan-shaped in FIG. 1 and includes multiple ultrasound beams $B_{1...k}$ that define image plane 12. Note that a fan-shaped beam is illustrated in FIG. 1 for the purposes of illustration only and that the invention is not limited to a particular shape of ultrasound field. Beamforming ultrasound imaging system 15 may also include electronic driver and receiver circuitry (not shown) that is configured to amplify and/or to adjust the phase of signals transmitted by or received by 2D ultrasound imaging probe 18 in order to generate and detect ultrasound signals in beams $B_{1...k}$. The electronic driver and receiver circuitry may thus be used to steer the emitted and/or received ultrasound beam direction.

In-use, beamforming ultrasound imaging system 15 is operated in the following way. An operator may plan an ultrasound procedure via imaging system interface ISI. Once an operating procedure is selected, imaging system interface ISI triggers imaging system processor ISP to execute application-specific programs that generate and interpret the signals transmitted to and detected by 2D ultrasound imaging probe 18. Beamforming ultrasound imaging system 15 may also include a memory (not shown) for storing such programs. The memory may for example store ultrasound beam control software that is configured to control the sequence of ultrasound signals transmitted by and/or received by ultrasound imaging probe 18. Image reconstruction unit IRU, which may alternatively form part of imaging system processor ISP, reconstructs data received from the ultrasound imaging probe 18 into an image corresponding to image plane 12 and which thus intercepts volume of interest VOI, and subsequently displays this image on display DISP. The reconstructed image may for example be an ultrasound Brightness-mode "B-mode" image, otherwise known as a "2D mode" image, a "C-mode" image or a Doppler mode image, or indeed any ultrasound planar image.

Also shown in FIG. 1 is a medical needle 11 as an exemplary interventional device, and a first embodiment of the invention 10 that may be used to track the position of distal end 11a, i.e. an interventional device feature, of medical needle 11 respective image plane 12 of beamforming ultrasound imaging system 15. The first embodiment of the invention 10 includes image reconstruction unit IRU, position determination unit PDU, icon providing unit IPU, and image fusion unit IFU. These units are in communication with one another as illustrated by the interconnecting arrows. It is also contemplated that one or more of units PDU, IPU, IFU may be incorporated within a memory or a processor of beamforming ultrasound imaging system 15, for example within a memory or a processor that provides the functionality of units IRU and ISP. Medical needle 11 that is tracked, includes ultrasound transducer 16 that is positioned at a predetermined distance Lp from distal end 11a of interventional device 11.

In-use, the position of interventional device 11, or more specifically that of ultrasound transducer 16 attached thereto, is computed respective image plane 12 by position determination unit PDU based on ultrasound signals transmitted between ultrasound transceiver array 14 and ultrasound detector 16.

In one configuration ultrasound transducer 16 is a detector that receives ultrasound signals corresponding to beams $B_{1...k}$. Position determination unit PDU identifies the position of ultrasound transducer 16 by correlating the ultrasound signals emitted by the ultrasound transceiver array with the ultrasound signals detected by ultrasound transducer 16. More specifically this correlation determines the best fit position of ultrasound transducer 16 respective image plane 12 based on i) the amplitudes of the ultrasound signals corresponding to each beam $B_{1 \ldots k}$ that are detected by ultrasound transducer 16 and ii) based on the time delay, i.e. time of flight, between emission of each beam $B_{1 \ldots k}$ and its detection by ultrasound transducer 16. This may be illustrated as follows. When ultrasound transducer 16 is in the vicinity of image plane 12, ultrasound signals from the nearest of beams $B_{1 \ldots k}$ to the transducer will be detected with a relatively larger amplitude whereas more distant beams will be detected with relatively smaller amplitudes. Typically the beam that is detected with the largest amplitude is identified as the one that is closest to ultrasound detector 16. This defines the in-plane angle $\Theta_{IPA}$ between ultrasound transceiver array 14 and ultrasound transducer 16. The range between the respective emitter in ultrasound transceiver array 14 and ultrasound transducer 16 depends upon the time delay, i.e. the time of flight, between the emission of a beam $B_{1 \ldots k}$ and its subsequent detection. The range is determined by multiplying the time delay by the speed of ultrasound propagation. Thus, the range and in-plane angle can be used to identify the best-fit position of ultrasound transducer 16 respective image plane 12.

In another configuration ultrasound transducer 16 is an emitter that emits one or more ultrasound pulses. Such pulses may for example be emitted during tracking frames that are interleaved between the usual imaging frames of ultrasound imaging system 15. In such a tracking frame the ultrasound transceiver array 14 may operate in a receive-only mode in which it listens for ultrasound signals originating from the vicinity of image plane 12. Ultrasound transceiver array 14 is thus configured as a one-way receive-only beamformer. Position determination unit PDU identifies from which beam of beams $B_{1 \ldots k}$ the pulse(s) originated based on the ultrasound signals emitted by ultrasound transducer 16 and those detected by ultrasound transceiver array 14. As in the configuration above, position determination unit PDU may use a correlation procedure that, based on the maximum amplitude and time of flight, identifies the closest beam to the point at which the ultrasound signal was emitted, and the range to its emitter. Thus, when ultrasound transducer 16 is an emitter, a correlation procedure may again be used to determine the best-fit position of ultrasound detector 16 respective image plane 12 for each tracking frame.

In another configuration ultrasound transducer 16 may be configured to act as both a receiver and an emitter, or include both a receiver and an emitter. In this configuration ultrasound transducer 16 may be triggered to emit one or more ultrasound pulses upon receipt of an ultrasound signal from ultrasound transceiver array 14; optionally following a delay that is equal to one or more frame periods of ultrasound imaging system 15. In this way the pulse(s) emitted by ultrasound transducer 16 during an imaging mode are received by ultrasound transceiver array 14 in the form of an echo in the reconstructed ultrasound at an in-plane angular position, i.e. in an image line, that corresponds to the triggering beam $B_{1 \ldots k}$. Ultrasound transducer 16 thus appears as a bright spot in the reconstructed image. Position determination unit PDU may subsequently identify this bright spot in the reconstructed image and thus compute a position of ultrasound transducer 16 respective image plane 12.

In yet another configuration not illustrated in FIG. 1, ultrasound imaging probe 18 further includes at least three ultrasound emitters that are attached to the ultrasound imaging probe 18. The at least three ultrasound emitters are in communication with position determination unit PDU. Moreover the position determination unit PDU is configured to compute a position of the ultrasound transducer 16 respective the image plane 12 based on ultrasound signals transmitted between the at least three ultrasound emitters attached to the ultrasound imaging probe 18, and the ultrasound transducer 16. In this configuration position determination unit PDU determines the distance between each emitter and ultrasound transducer 16 based on the time of flight of ultrasound signals emitted by each emitter. The position of ultrasound transducer 16 is subsequently determined using triangulation. This provides the position of ultrasound transducer 16 in three dimensions respective ultrasound imaging probe 18, or more specifically respective image plane 12 since the at least three emitters are attached to the ultrasound imaging probe 18. Emitters are preferred in this configuration because the supply of high power ultrasound signals to the emitters, necessary for accurate positioning over a large range, is simpler when the emitters are proximate ultrasound imaging probe 18. This arrangement is thus preferred in contrast to locating a high power emitter on the interventional device 11. In-use, the position of interventional device 11, or more specifically that of ultrasound transducer 16 attached thereto, is thus computed respective image plane 12 by position determination unit PDU based on ultrasound signals transmitted between the at least three emitters and ultrasound detector 16.

Thus position determination unit PDU illustrated in FIG. 1 may be used in any of the above configurations to compute a position of ultrasound transducer 16 respective image plane 12 based on ultrasound signals transmitted between ultrasound imaging probe 18 and ultrasound transducer 16.

FIG. 1 also includes icon providing unit IPU which is configured to provide a first icon Cde. The first icon Cde is indicative of a circular zone with a radius corresponding to the predetermined distance Lp between the ultrasound transducer 16 and the distal end 11a of medical needle 11. Icon providing unit IPU may for example be implemented by means of a processor, a memory, look-up table or another form of data storage. In a preferred implementation the first icon Cde is a circle. However, other shapes may also be used to indicate a circular zone including e.g. a circular arrangement of dots or dashes, a circular arrangement of radially-directed lines or arrows, the tips of which indicate a circular zone. Icon providing unit IPU thus provides the data necessary to render an ultrasound image with the desired icon. Optionally, Icon providing unit IPU may store additional data regarding the interventional device or the interventional device feature such as the type or size or a dimension of the interventional device or the feature, e.g. a needle diameter, or the orientation of the interventional device feature respective the interventional device. Optionally this data may also be rendered in the ultrasound image together with the first icon.

FIG. 1 also includes image fusion unit IFU. Image fusion unit IFU is configured to provide a fused image comprising the reconstructed ultrasound image RUI that is provided by image reconstruction unit IRU together with first icon Cde. In the fused image the first icon Cde is centered in the reconstructed ultrasound image RUI at an insertion point corresponding to a projection of the position of the ultrasound transducer 16 onto the image plane 12. Image fusion unit IFU may for example be implemented by means of a processor. The fusion may be performed e.g. by making an overlay of the first icon onto the reconstructed ultrasound image RUI, or by changing the contrast or color of the reconstructed ultrasound image RUI at the position of the icon and so forth.

Each of the units in FIG. 1: image fusion unit IFU, icon providing unit IPU, position determination unit PDU, and image reconstruction unit IRU may be provided by one or more processors including instructions to perform their respective function. Moreover, one or more of these units may be provided by imaging system processor ISP of beamforming ultrasound imaging system 15.

Figure 2:
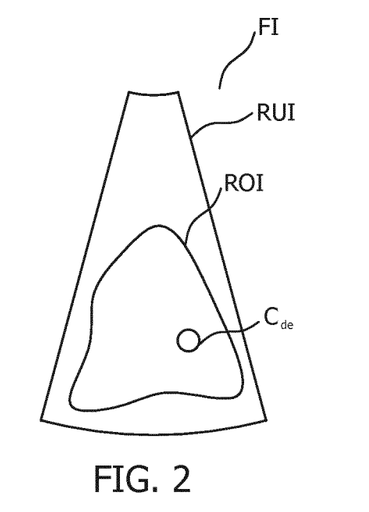
FIG. 2 illustrates a fused image FI that includes a reconstructed ultrasound image RUI and a first icon Cde.

FIG. 2 illustrates a fused image FI that includes a reconstructed ultrasound image RUI and a first icon Cde. Fused image FI may be generated by the first embodiment of the invention 10 during the imaging of region of interest ROI. In FIG. 2, the first icon Cde is centered in the reconstructed ultrasound image RUI at an insertion point corresponding to a projection of the position of the ultrasound transducer 16 onto image plane 12 of FIG. 1.

In so doing, the position of ultrasound transducer 16 is made visible to a user of the system by means of the center of the circular zone indicated by the first icon Cde in FIG. 2. In the arrangement shown in FIG. 1 and FIG. 2 the ultrasound transducer is in-plane and thus the insertion point as-determined by the projection coincides with the actual position of ultrasound transducer 16 on image plane 12. However, as described above, a user is typically more interested in the position of the distal end 11a of the medical needle 11 than the position of the detector itself. Advantageously, the position of the distal end 11a is indicated by the perimeter of the circular zone indicated by the first icon Cde. This is because the radius of the circular zone corresponds to the predetermined distance Lp between the ultrasound transducer 16 and the distal end 11a, and because both the ultrasound transducer 16 and the distal end 11a are in-plane; i.e. they lie in image plane 12. When a single ultrasound transducer 16 is attached to the medical needle 11 to track its position the exact radial direction in the fused image FI along which the interventional device feature is located respective the ultrasound transducer 16 is indeterminable. The system however indicates that the distal end 11a lies predetermined distance Lp from ultrasound detector 16; i.e. somewhere around the perimeter of the circular zone indicated by the first icon. This is valuable information to a user in narrowing-down the exact position of distal end 11a. Consequently the system provides localization of the position of the distal end 11a of medical needle 11 when a single ultrasound transducer 16 is attached to the medical needle. Moreover, a user will typically know the approximate trajectory of medical needle 11 and will thus know whether they are in the in-plane scenario illustrated in FIG. 1. Based on the user's progression of the needle and this approximate trajectory, the user will also know approximately which part of the perimeter of the circular zone the distal end of the medical needle is actually located. Moreover the user will be aware of this trajectory from intermittent reconstructed ultrasound images of the shaft of medical needle 11. Thus the user can augment the information provided by first icon Cde in order to identify more precisely where on the perimeter of the circular zone the distal end 11a lies.

Figure 3:
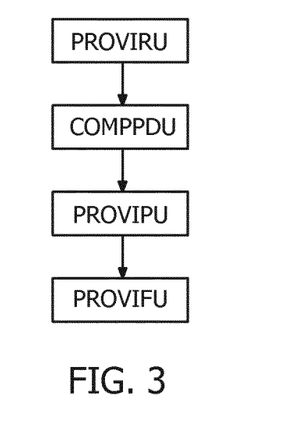
FIG. 3 illustrates various method steps that may be associated with any of the embodiments of the invention.

FIG. 3 illustrates various method steps that may be associated with any of the embodiments of the invention. These steps include: a) Providing PROVIRU, with an image reconstruction unit IRU, a reconstructed ultrasound image RUI corresponding to an image plane 12 defined by the ultrasound imaging probe 18; b) Computing COMPPDU, with a position determination unit PDU, a position of the ultrasound transducer 16 respective the image plane 12 based on ultrasound signals transmitted between the ultrasound imaging probe 18 and the ultrasound transducer; c) providing PROVIPU, with an icon providing unit IPU, a first icon Cde indicative of a circular zone with a radius corresponding to the predetermined distance Lp between the ultrasound transducer 16 and the interventional device feature 11a; and d) providing PROVIFU, with an image fusion unit IFU, a fused image comprising the reconstructed ultrasound image RUI and the first icon Cde, wherein the first icon Cde is centered in the reconstructed ultrasound image RUI at an insertion point corresponding to a projection of the position of the ultrasound transducer 16 onto the image plane 12.

The method steps illustrated in FIG. 3, optionally including other method steps described herein, may be stored on a computer program product as instructions that are executable by a processor. The computer program product may be provided by dedicated hardware, or hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk read only memory "CD-ROM", compact disk read/write "CD-R/W", Blu-Ray™ and DVD.

Whilst the first embodiment of the invention illustrated in FIG. 1 has been described in terms of an in-plane scenario in which the ultrasound transducer 16 is in image plane 12, the system also finds application in a so-called out-of-plane scenario in which ultrasound transducer 16 lies outside the image plane.

Figure 4:
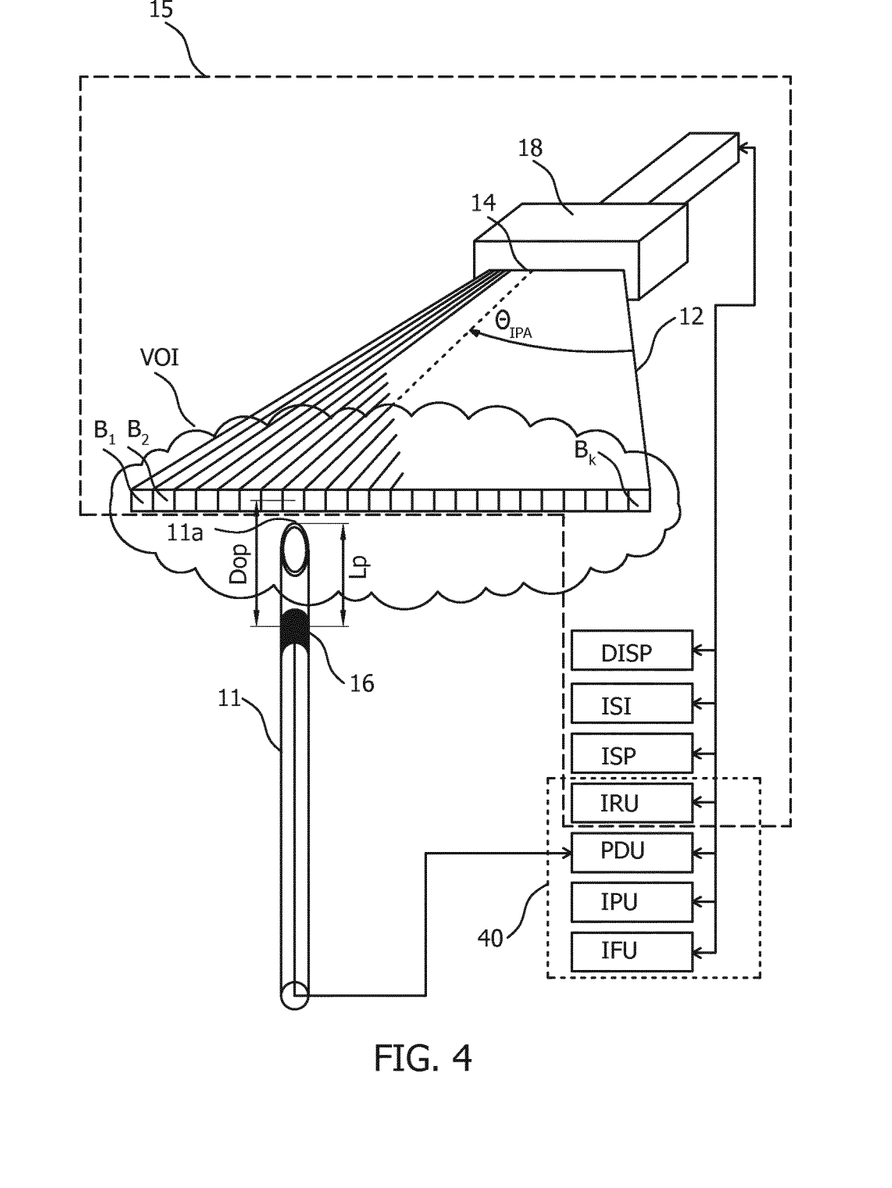
FIG. 4 illustrates a beamforming ultrasound imaging system 15 in combination with an interventional device 11 and a second embodiment of the invention 40.

FIG. 4 illustrates a beamforming ultrasound imaging system 15 in combination with an interventional device 11 and a second embodiment of the invention 40. Except where described to the contrary, features of FIG. 4 having the same references as FIG. 1 perform corresponding functions. In FIG. 4 ultrasound transducer 16 is located at a distance Dop from image plane 12. Dop is thus an out-of-plane distance. As in FIG. 1, the beamforming ultrasound imaging system 15 in FIG. 4 is a 2D ultrasound imaging probe 18. In practice image plane 12 has a finite thickness and typically generates an ultrasound field for a short distance in an out-of-plane direction. Thus when ultrasound transducer 16 is a detector, even when this detector is slightly away from image plane 12, i.e. out-of-plane, it will detect ultrasound signals corresponding to beams $B_{1 \ldots k}$ in the same way as described above for the in-plane scenario of FIG. 1. Likewise, when ultrasound transducer 16 is an emitter, even when this emitter is slightly away from image plane 12, ultrasound transceiver array 14 will be sensitive to ultrasound emissions from this emitter. In other words, even when ultrasound transceiver array 14 is a linear array of a 2D ultrasound imaging probe the position of ultrasound detector 16 respective image plane 12 may be computed by position determination unit PDU when it is a distance Dop from this plane. In one configuration, position determination unit PDU may determine out-of-plane distance Dop of detector 16 based on a model of the expected variation in ultrasound signal intensity with out-of-plane distance Dop. The model may for example describe the variation in ultrasound signal intensity with out-of-plane distance Dop as a Gaussian function. Thus the position determination unit in FIG. 4 may operate in the following manner: i) determine the in-plane angle CI IPA of ultrasound detector 16 based on the beam $B_{1 \ldots k}$ that is detected with maximum intensity ii) determine the range between the corresponding emitter in ultrasound transceiver array 14 and detector 16 based on the time delay between emission and detection i.e. the time of flight, of the ultrasound signal in the maximum-intensity beam iii) compute the out of plane distance Dop based on a model of the variation in signal intensity with out-of-plane distance Dop for the determined range. A similar procedure may be used when ultrasound transducer 16 is an emitter. When ultrasound transceiver array 14 is a 2D array the out-of-plane distance Dop may alternatively be determined using time of flight and triangulation from three positions on the transceiver array.

In the second embodiment of the invention illustrated in FIG. 4; when ultrasound transducer 16 is out-of-plane, the first icon Cde is centered in the reconstructed ultrasound image RUI at an insertion point corresponding to a projection of the position of the ultrasound transducer 16 onto the image plane 12.

Whilst the second embodiment of FIG. 4 is described above in terms of a position determination unit PDU that determines the position of ultrasound transducer 16 including the out of plane distance Dop based on ultrasound signals detected by the ultrasound transducer 16 from ultrasound transceiver array 14, it will be appreciated that this second embodiment may alternatively operate in the following manner. Ultrasound imaging probe 18 may further include at least three ultrasound emitters that are attached to the ultrasound imaging probe 18. Moreover the position determination unit PDU is configured to compute a position of the ultrasound transducer 16 respective the image plane 12 based on ultrasound signals transmitted between the at least three ultrasound emitters attached to the ultrasound imaging probe 18, and the ultrasound transducer 16. In this configuration position determination unit PDU determines the distance between each emitter and ultrasound transducer 16 based on the time of flight of ultrasound signals emitted by each emitter. The position of ultrasound transducer 16 is subsequently determined using triangulation. This provides the position of ultrasound transducer 16 in three dimensions respective ultrasound imaging probe 18, or more specifically respective image plane 12. Thus in contrast to determining the out of plane distance Dop from the ultrasound signals of the ultrasound transceiver array 14, here the out of plane distance Dop is determined using the 3D position data that is provided by ultrasound transducer 16 from the at least three ultrasound emitters. This out of plane distance Dop may be calculated, for example, by calculating the shortest distance to image plane 12.

Figure 5:
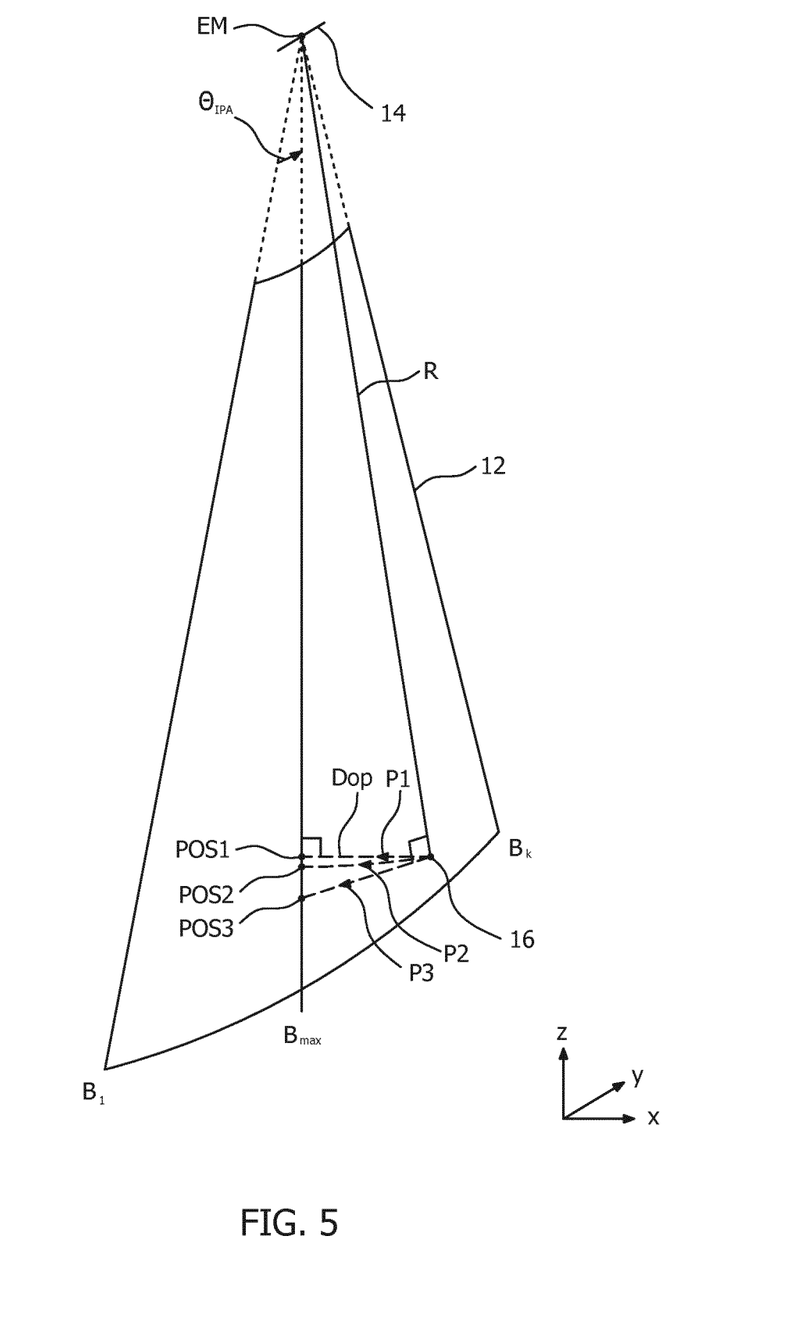
FIG. 5 illustrates various projections of the position of ultrasound transducer 16 onto image plane 12 when it is positioned at an out-of-plane distance Dop: i) by projecting P1 in a direction that is normal to the image plane ii) by projecting P2 the range R between emitter EM and the ultrasound transducer 16 onto image plane 12 at the in-plane angle $\Theta_{IP4}$ for the beam $B_{max}$ detected with maximum intensity, and iii) by projecting P3 in a direction that is perpendicular to the range R direction to emitter EM and perpendicular to ultrasound transceiver array 14.

FIG. 5 illustrates various projections of the position of ultrasound transducer 16 onto image plane 12 when it is positioned at an out-of-plane distance Dop: i) by projecting P1 in a direction that is normal to the image plane ii) by projecting P2 the range R between emitter EM and the ultrasound transducer 16 onto image plane 12 at the in-plane angle $\Theta_{IPA}$ for the beam $B_{max}$ detected with maximum intensity, and iii) by projecting P3 in a direction that is perpendicular to the range R direction to emitter EM and perpendicular to the ultrasound transceiver array 14. Depending on which projection of P1, P2, P3 is used, this results in a corresponding insertion point POS1, POS2, POS3 in the reconstructed ultrasound image. Any of the projections illustrated in FIG. 5 may be used in the second embodiment of the invention illustrated in FIG. 4.

In a preferred implementation the projection is in a direction that is normal to image plane 12; i.e. P1 in FIG. 5. This provides an insertion point at POS1 which is the closest point to the actual, offset position of detector 16. Alternatively the projection may for example project the range R between the emitter EM and the ultrasound transducer 16 onto the image plane at the in-plane angle for the beam $B_{1 \ldots k}$ detected with maximum intensity; in other words swing range R onto image plane 12 at the in-plane angle $\Theta_{IPA}$ for the beam $B_{max}$ detected with maximum intensity; i.e. P2 in FIG. 5. Alternatively the projection may for example be at an angle, preferably 90 degrees, to the range direction to the emitter and perpendicular to the linear array; i.e. P3 in FIG. 5. When ultrasound detector 16 is in image plane 12 it is noted that the same insertion point is achieved for each of the projections in FIG. 5.

In the second embodiment, image fusion unit IFU uses the computed out-of-plane distance Dop to provide in the fused image a second icon Cop. The out of plane distance Dop is preferably the shortest distance to image plane 12, i.e. projection P1 in FIG. 5 is used. However when other projections e.g. P2, P3 are used the out-of-plane distance may correspond to the length of a vector connecting the actual position to the projected position. It is noted that for small out of plane distances Dop the differences between each of the projections is negligible. The second icon Cop is indicative of a circular zone and has a radius that varies in accordance with the out-of-plane distance Dop. In so doing, a fused image is provided by the second embodiment that includes the reconstructed ultrasound image RUI, first icon Cde, and second icon Cop. The first icon has a fixed radius and the second icon has variable radius. This is illustrated in FIG. 6.

Figure 6A:
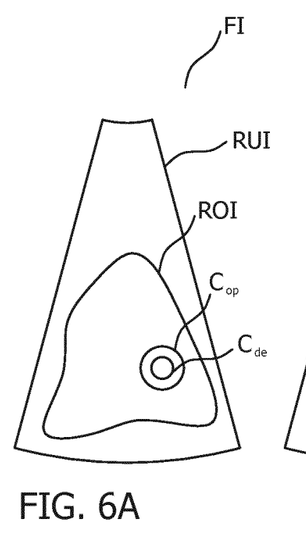
FIG. 6A, FIG. 6B, FIG. 6C each illustrate a fused image FI that includes a reconstructed ultrasound image RUI, a first icon Cde indicative of a circular zone with a radius corresponding to the predetermined distance Lp between the ultrasound transducer 16 and the distal end 11a of medical needle 11, and a second icon Cop indicative of a circular zone with a radius that varies in accordance with the out-of-plane distance Dop.
Figure 6B:
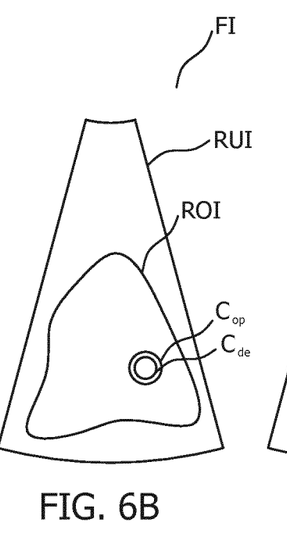
Figure 6C:
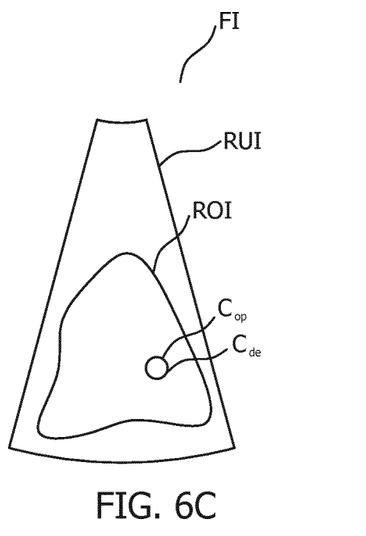

FIG. 6A, FIG. 6B, FIG. 6C each illustrate a fused image FI that includes a reconstructed ultrasound image RUI, a first icon Cde indicative of a circular zone with a radius corresponding to the predetermined distance Lp between the ultrasound transducer 16 and the distal end 11a of medical needle 11, and a second icon Cop indicative of a circular zone with a radius that varies in accordance with the out-of-plane distance Dop. First icon Cde and second icon Cop share a common center. Fused image FI may be generated during imaging of region of interest ROI. The first icon Cde in FIG. 6A, Fig. B, Fig. C is centered in the reconstructed ultrasound image RUI at an insertion point corresponding to a projection of the position of the ultrasound transducer 16 onto image plane 12 of FIG. 5. In so doing, the position of ultrasound transducer 16 is indicated a system user by means of the center of the circular zone indicated by the first icon Cde. As described above in relation to FIG. 1, a user is however typically more interested in the position of the distal end 11a of medical needle 11 than the position of the ultrasound transducer 16. In the out-of-plane situation illustrated by FIG. 4 ultrasound transducer 16 and distal end 11a both lie along a line that passes normally through image plane 12. In this scenario, because first icon Cde and second icon Cop share a common center, both distal end 11a and ultrasound transducer 16 are located at the common center of Cop and Cde. Moreover, the relative sizes of Cop and Cde indicate the proximity of distal end 11a to image plane 12. When distal end 11a is in image plane 12, i.e. coincides with image plane 12, Cop and Cde have the same size. This helps a user in guiding distal end 11a of medical needle 11 to a feature within region of interest ROI in image plane 12. Thus in FIG. 6A distal end 11a is somewhat out-of-plane, and Dop>Lp, as indicated by the radius of circle of Cop exceeding that of Cde. As distal end 11a is advanced towards image plane 12 the difference between the radii of the circles Cop and Cde decreases, as illustrated in FIG. 6B. When the tip of the interventional device is in-plane the radii of the circles Cop and Cde are the same and the perimeters of the circles coincide, as illustrated in FIG. 6C.

In another scenario that is not illustrated, distal end 11a of medical device 11 lies in image plane 12 and ultrasound transducer 16 is located above or below image plane 12 along a line passing through distal end 11a and at an acute angle to the image plane. Here the fused image includes a first icon Cde which is centered at the position of ultrasound transducer 16 as-projected onto image plane 12. Con-centric with Cde, and within Cde, is second icon Cop indicating the out-of-plane distance Dop. Distal end 11a now lies somewhere within the circular zone indicated by the first icon Cde. Thus, the first icon defines a portion of the image plane corresponding to a range of possible positions of the interventional device feature. In this scenario, the combination of the two icons again assists a user in guiding distal end 11a respective image plane 12. Moreover, the guidance provided by the system may be supplemented by a system user's knowledge to more precisely locate the position of distal end 11a. For example, partial images of the interventional device trajectory obtained from ultrasound reflections in the usual way under ultrasound imaging system may allow the user to identify more precisely where distal end 11a lies.

In either the first or the second embodiments, the icons may take various forms. In a preferred implementation each icon is a circle that is overlaid onto the reconstructed ultrasound image. Preferably only the perimeter of the circle is displayed in the fused image since this offers minimal disturbance of the ultrasound image itself. Preferably the perimeter of the circle is white or black or colored in order to present a high contrast with the nearby region of interest. The circle perimeter may be a continuous line or formed from dashed lines or dots. Other implementations are also suitable, for example each icon may take the form of a partially-transparent circular zone, or alternatively markers may be used to indicate a circular zone, for example a circular arrangement of radially-directed lines or arrows may be used.

In one example implementation that may be used with the second embodiment the image fusion unit IFU is further configured to cause the appearance of at least one of the first icon Cde and the second icon Cop to change when the out of plane distance Dop is less than or equal to the predetermined distance Lp. Since, as described above, a user is typically interested in determining when the distal end 11a of medical needle 11 is in the image plane, this feature can be used to alert a user to this situation automatically, thereby allowing the user to focus on other tasks. The appearance of an icon may be changed by for example changing its color, changing its contrast and so forth. In one example implementation an icon has a perimeter, and the appearance of at least one of the first icon Cde and the second icon Cop may be configured to change by at least one of: i) changing a color of the perimeter of the first icon Cde or the second icon Cop; ii) changing a contrast of the perimeter of the first icon Cde or the second icon Cop; iii) indicating the perimeter of the first icon Cde or the second icon Cop with dashes; iv) causing the perimeter of the first icon Cde or the second icon Cop to pulse; i.e. to change its contrast, color or intensity over time.

In one example implementation that may be used with the second embodiment the radius of the second icon Cop has a minimum value that is equal to the radius of the first icon Cde, and the radius of the second icon Cop is limited to the minimum value when the out-of-plane distance Dop is less than or equal to the predetermined distance Lp. The second icon Cop may even be completely removed from the fused image when the out-of-plane distance Dop is less than or equal to the predetermined distance Lp. This feature prevents the user from sub-consciously making continuous small adjustments to the interventional device position in order to make the radius of the second icon Cop exactly equal to the radius of the first icon Cde. Such adjustments have been found to be mentally tiring for a user, and thus by so limiting, or truncating, the minimum size of the second icon this feature allows a user to focus on other tasks.

Figure 7:
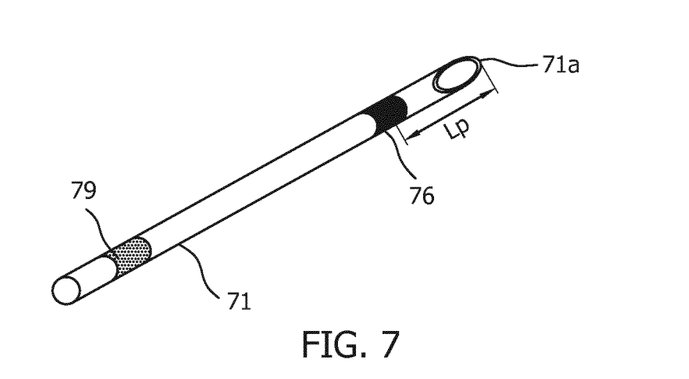
FIG. 7 illustrates an intervention device 71 that is suitable for use with either the first embodiment or the second embodiment of the invention.

FIG. 7 illustrates an intervention device 71 that is suitable for use with either the first embodiment or the second embodiment of the invention. Interventional device 71 includes interventional device feature 71a, ultrasound transducer 76 and optional data carrier 79. Ultrasound transducer 76 is attached to interventional device 71 at predetermined distance Lp from interventional device feature 71a. Data carrier 79 comprises data representative of the predetermined distance Lp. Ultrasound transducer 76 may be a transmitter or a receiver or may include a transmitter and a receiver, or may be adapted for both transmitting and receiving ultrasound signals. Whilst interventional device 71 is illustrated as a medical needle with interventional device feature as distal end 71a, the interventional device and the feature may be any of those disclosed herein.

The data, when received by the icon providing unit IPU of system 10, 40, causes the icon providing unit IPU to provide a first icon Cde indicative of a circular zone with a radius corresponding to the predetermined distance Lp between the ultrasound transducer 76 and the interventional device feature 71a. Data carrier 79 thus carries data representing the size of first icon Cde. Optionally the data carrier may include a size or a dimension of the interventional device or the feature, e.g. a needle diameter, or the orientation of the interventional device feature respective the interventional device. Optionally this data may also be rendered in the ultrasound image together with the first icon. The data carrier may itself store the data representing the size of the first icon, for example by storing the radius of the circular zone corresponding to the predetermined distance Lp, for example in digital form, or the data carrier may store the type (T) of the interventional device, and the actual data regarding the predetermined distance Lp being extracted from a look-up table stored in the system 10, 40, for example in icon providing unit IPU. In one implementation the data is received wirelessly by icon providing unit IPU from data carrier 79. The data carrier may thus be, for example, an RFID chip, or a linear or matrix barcode or a QR code and so forth. In another example the data is received via wired communication with between data carrier 79 and icon providing unit IPU. Thus the data carrier may, for example, be a memory associated with the interventional device. Thus the data carrier may in general be an RFID chip, or a barcode such as a linear or matrix barcode or a QR code, a memory or indeed any machine-readable data carrier. Icon providing unit IPU may thus include a reader for reading the data in the data carrier such as a barcode reader, an RFID reader, or a data reader in general. Alternatively a user may input this data manually to system 10 by means of imaging system interface ISI from which it is received by icon providing unit IPU. Data carrier 79 may be attached to interventional device 71 by various known means including adhesives, or it may be applied to interventional device 71 by printing, etching, and the like. Also, whilst illustrated as being disposed on the interventional device 71, data carrier 79 may alternatively be positioned on the packaging of interventional device 71, for example for sterility reasons.

Thus, when interventional device 71 of FIG. 7 is used with either the first or the second embodiment of the invention, i.e. item 10 in FIG. 1, item 40 in FIG. 4 the data received by the icon providing unit IPU enables the technical effect of improved determination of the position of the interventional device respective the image plane of the beamforming ultrasound imaging system.

Ultrasound transducer 76 illustrated in FIG. 7 and as item 16 in FIGS. 1 and 4 may be provided by a variety of piezoelectric materials, both hard and soft piezoelectric materials being suitable. Moreover, Micromachined Electromechanical Structures, i.e. MEMS devices such as Capacitive Machined Ultrasound Transducers, i.e. CMUT, devices are also suitable. When the ultrasound transducer is a detector, preferably it is formed from Polyvinylidene fluoride, otherwise known as PVDF whose mechanical properties and manufacturing processes lend themselves to attachment to curved surfaces such as needles. Alternative materials include a PVDF co-polymer such as polyvinylidene fluoride trifluoroethylene, a PVDF ter-polymer such as P(VDF-TrFE-CTFE). Preferably the ultrasound transducer is wrapped around an axis of the interventional device in order to provide sensing around 360 degrees of rotation about the axis although this need not always be the case. Moreover, ultrasound transducer 76 may include various wires or a wireless communication module that are not shown in FIG. 7 for communicating detected ultrasound signals with position determination unit PDU in FIG. 1 and FIG. 4.

Optionally, data carrier 79 in FIG. 7 may include one or more data fields indicative of one or more of the following parameters: a length of ultrasound transducer 76 along an axis extending between the ultrasound transducer and the distal end of the interventional device; a width of ultrasound transducer 76 perpendicular to an axis extending between the ultrasound transducer and the distal end of the interventional device. When the data field(s) are received by icon providing unit IPU of system 10, 40 the parameters may be indicated in a fused image FI generated by image fusion unit IFU. The respective parameter may for example be indicated in the form of a thickness of the perimeter of the first circle Cop or a thickness of the perimeter of the second circle Cde, or in the form of a third circle having a radius that corresponds to the extent of the ultrasound transducer and which shares a common center with the second circle Cde. In this way the perimeter thickness, or the extent of the third circle is indicative of the uncertainty of the position of the interventional device arising from the ultrasound transducer's finite length and width. Either of these data fields may be stored on data carrier 79 of interventional device 71 and thus received therefrom by icon providing unit IPU.

In summary, a system for indicating a position of an interventional device feature 11a of an interventional device respective an image plane defined by an ultrasound imaging probe of a beamforming ultrasound imaging system has been described in which the position of the interventional device feature is determined based on ultrasound signals transmitted between the ultrasound imaging probe and an ultrasound transducer attached to the interventional device at a predetermined distance from the interventional device feature. A position determination unit computes a position of the ultrasound transducer respective the image plane. An icon providing unit provides a first icon indicative of a circular zone with a radius corresponding to the predetermined distance. An image fusion unit provides a fused image comprising a reconstructed ultrasound image from the beamforming ultrasound imaging system and the first icon. The first icon is centered in the reconstructed ultrasound image at an insertion point corresponding to a projection of the position of the ultrasound transducer onto the image plane.

Whilst the invention has been illustrated and described in detail in the drawings and foregoing description in relation to a medical needle, such illustrations and descriptions are to be considered illustrative or exemplary and not restrictive; the invention is not limited to the disclosed embodiments and can be used for determining the position of interventional devices in general. Moreover it is to be understood that the various examples and embodiments illustrated herein may be combined in order to provide various systems, devices and methods for indicating a position of an interventional device feature of an interventional device respective an image plane of a beamforming ultrasound imaging system.

The invention claimed is:

1. A system for indicating a position of an interventional device feature of an interventional device, the system comprising:

an ultrasound imaging probe of a beamforming ultrasound imaging system;

an interventional device configured with an ultrasound transducer and an interventional device feature, wherein the ultrasound transducer is attached to the interventional device at a predetermined distance from the interventional device feature;

an image reconstruction processor configured to provide a reconstructed ultrasound image corresponding to an image plane defined by the ultrasound imaging probe;

a position determination processor configured to (i) compute a position of the ultrasound transducer respective the image plane based on ultrasound signals transmitted between the ultrasound imaging probe and the ultrasound transducer and (ii) project the position of the ultrasound transducer onto the image plane;

an icon providing processor configured to provide a first icon indicative of a circular zone with a radius corresponding to the predetermined distance between the ultrasound transducer and the interventional device feature; and an image fusion processor configured to provide a fused image comprising the reconstructed ultrasound image and the first icon, wherein the image fusion processor is configured to provide the fused image by: (i) locating, in the reconstructed ultrasound image, an insertion point corresponding to the projected position of the ultrasound transducer onto the image plane and (ii)

centering the first icon at the insertion point corresponding to the projected position of the ultrasound transducer onto the image plane so that the first icon indicates possible positions of the interventional device feature within the image plane.

2. The system according to claim 1, wherein the first icon defines a portion of the image plane corresponding to a range of possible positions of the interventional device feature.

3. The system according to claim 1, wherein the position computed by the position determination processor includes an out-of-plane distance corresponding to a distance between the ultrasound transducer and the image plane; and wherein the image fusion processor is further configured to provide in the fused image a second icon indicative of a circular zone with a radius that varies in accordance with the out-of-plane distance.

4. The system according to claim 3, wherein the first icon and the second icon share a common center.

5. The system according to claim 3, wherein the image fusion processor is further configured to cause the appearance of at least one of the first icon and the second icon to change when the out-of-plane distance is less than or equal to the predetermined distance.

6. The system according to claim 5, wherein the first icon and the second icon each has a perimeter, and wherein the appearance of at least one of the first icon and the second icon is configured to change by at least one of:
changing a color of the perimeter of the first icon or the second icon;
changing a contrast of the perimeter of the first icon or the second icon;
indicating the perimeter of the first icon or the second icon with dots or dashes; and/or
causing the perimeter of the first icon or the second icon to pulse over time.

7. The system according to claim 3, wherein the radius of the second icon has a minimum value that is equal to the radius of the first icon, and wherein the radius of the second icon is limited to the minimum value when the out-of-plane distance is less than or equal to the predetermined distance.

8. The system according to claim 1, wherein the interventional device feature is one of the following:
a distal end of the interventional device;
an opening of a channel in the interventional device;
a biopsy sampling point of the interventional device;
a cutting edge of the interventional device;
a sensor of the interventional device;
a surgical tool integrated into the interventional device;
a drug delivery point of the interventional device; or
an energy delivery point of the interventional device.

9. The system according to claim 8, wherein the ultrasound imaging probe further comprises either i) an ultrasound transceiver array, or ii) at least three ultrasound emitters attached to the ultrasound imaging probe, and wherein the position determination processor is configured to compute the position of the ultrasound transducer respective the image plane based on ultrasound signals transmitted between the ultrasound transceiver array and the ultrasound transducer, or between the at least three ultrasound emitters attached to the ultrasound imaging probe and the ultrasound transducer, respectively.

10. The system according to claim 9, wherein the ultrasound imaging probe is selected from the group consisting of: a 2D ultrasound imaging probe, a 3D ultrasound imaging probe, a transrectal ultrasonography probe, an intravascular ultrasound probe, a transesophageal probe, a transthoracic probe, a transnasal probe, and an intracardiac probe.

11. The system according to claim 1, further comprising an interventional device having an ultrasound transducer attached thereto.

12. The system according to claim 1, wherein the interventional device is selected from the group consisting of: a medical needle, a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool, an ablation device, a tissue sealing device, a tissue cutting device, a drug delivery device, and an implantable device.

13. The system according to claim 12, wherein the interventional device has a data carrier that comprises data representative of the predetermined distance.

14. A method of indicating a position of an interventional device feature of an interventional device, the method comprising:
providing an interventional device configured with an ultrasound transducer and an interventional device feature, wherein the ultrasound transducer is attached to the interventional device at a predetermined distance from the interventional device feature;
providing, by an image reconstruction processor, a reconstructed ultrasound image corresponding to an image plane defined by an ultrasound imaging probe of a beamforming ultrasound imaging system;
computing, by a position determination processor, (i) a position of the ultrasound transducer respective the image plane based on ultrasound signals transmitted between the ultrasound imaging probe and the ultrasound transducer and (ii) a projection of the position of the ultrasound transducer onto the image plane;
providing, by an icon providing processor, a first icon indicative of a circular zone with a radius corresponding to the predetermined distance between the ultrasound transducer and the interventional device feature; and
providing, by an image fusion processor, a fused image comprising the reconstructed ultrasound image and the first icon, wherein the fused image is provided by (i) locating, in the reconstructed ultrasound image, an insertion point corresponding to the projected position of the ultrasound transducer onto the image plane and (ii) centering the first icon at the insertion point corresponding to the projected position of the ultrasound transducer onto the image plane so that the first icon indicates possible positions of the interventional device feature within the image plane.

15. A non-transitory computer-readable storage medium having stored a computer program comprising instructions which, when executed by a processor, cause the processor to:
provide a reconstructed ultrasound image corresponding to an image plane defined by an ultrasound imaging probe of a beamforming ultrasound imaging system, wherein the ultrasound imaging probe is in communication with an interventional device configured with an ultrasound transducer and an interventional device feature, wherein the ultrasound transducer is attached to the interventional device at a predetermined distance from the interventional device feature;
compute (i) a position of the ultrasound transducer respective the image plane based on ultrasound signals transmitted between the ultrasound imaging probe and the ultrasound transducer and (ii) a projection of the position of the ultrasound transducer onto the image plane;

provide a first icon indicative of a circular zone with a radius corresponding to the predetermined distance between the ultrasound transducer and the interventional device feature; and provide a fused image comprising the reconstructed ultrasound image and the first icon, wherein the fused image is provided by (i) locating, in the reconstructed ultrasound image, an insertion point corresponding to the projected position of the ultrasound transducer onto the image plane and (ii) centering the first icon at the insertion point corresponding to the projected position of the ultrasound transducer onto the image plane so that the first icon indicates possible positions of the interventional device feature within the image plane.

* * * * *